US00PP37424P2

(12) United States Plant Patent
Hansen

(10) Patent No.: US PP37,424 P2
(45) Date of Patent: May 12, 2026

(54) *PANICUM* GRASS NAMED 'Smoking Gun'

(50) Latin Name: ***Panicum* hybrid**
Varietal Denomination: Smoking Gun

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/831,964

(22) Filed: Dec. 11, 2025

(51) Int. Cl.
*A01H 5/12* (2018.01)
*A01H 6/46* (2018.01)

(52) U.S. Cl.
USPC ..... Plt./384

(58) Field of Classification Search
USPC ..... Plt./384
See application file for complete search history.

(56) References Cited

U.S. PATENT DOCUMENTS

PP29,142 P2 * 3/2018 Hansen ..... A01H 6/4642 Plt./360

* cited by examiner

*Primary Examiner* — Susan McCormick Ewoldt
*Assistant Examiner* — Zachariah Allan Kay

(57) ABSTRACT

A new and distinct plant of ornamental switch grass named *Panicum* 'Smoking Gun' with broad bluish-green foliage that retains it coloration into the fall. The foliage is upright to outwardly pointing with very little arching in the distal portion. The upright and dense culms produce tall plant with broadly-spreading airy panicles becoming tan seed heads that are retained into winter.

1 Drawing Sheet

Latin botanical classification: *Panicum* hybrid.
Variety denomination: 'Smoking Gun'.

STATEMENT REGARDING PRIOR DISCLOSURES UNDER 37 CFR 1.77(B)(6)

The claimed plant was first offer for sale to Prides Corner Farm by Walters Gardens, Inc. on Dec. 17, 2024. Walters Gardens, Inc. obtained *Panicum* 'Smoking Gun' and all information relating thereto, from the inventor. No plants of *Panicum* 'Smoking Gun' have been sold in this country or anywhere in the world, nor has any disclosure of the new plant been made, more than one year prior to the filing date of this application, and any sale or disclosure within one year was either derived directly or indirectly from the inventor.

BACKGROUND OF THE PLANT

*Panicum* 'Smoking Gun', hereinafter also referred by just the cultivar name 'Smoking Gun' and the "new plant", is a new and distinct cultivar of switch grass. The new plant originated from a cross between the proprietary, unnamed hybrid known only by the breeder code 17-6-x (not patented) with the proprietary, unnamed hybrid known only by the breeder code 17-2 (not patented) at a wholesale perennial nursery in Zeeland, Michigan in the summer of 2018. The seed was collected in the autumn of 2018 and sown the following spring. The individual seedling was initially selected from among many for further observation in the summer and fall of 2020 at which time it was assigned the breeder code 18-2-5 prior to giving the new plant a cultivar name.

The new plant has been successfully asexually propagated by division since fall of 2020 at the same wholesale perennial plant nursery and found to produce stable and identical plants that maintain the unique characteristics of the original plant in successive generations of asexual reproduction.

BRIEF SUMMARY OF THE PLANT

*Panicum* 'Smoking Gun' differs from its female parent, 17-6-x, in that the new plant is shorter and has more blue-green foliage that does not change over the growing season. The male parent, 17-2, is similar in leaf color but is significantly taller in habit with more arching foliage.

The nearest comparison varieties known to the inventor are: 'Blue Fountain' U.S. Plant Pat. No. 28,192, 'Apache Rose' U.S. Plant Pat. No. 29,142, 'Dallas Blues' U.S. Plant Pat. No. 11,202, 'Gun Smoke' U.S. Plant Pat. No. 32,373, and 'Niagara Falls' U.S. Plant Pat. No. 34,509.

The new plant is similar in leaf color and form but is significantly shorter than 'Blue Fountain' and a more cascading foliage habit and greyed reddish-purple seed heads before maturing to tan. 'Apache Rose' has more intense red in the seed heads, the leaves and habit are slightly shorter and develop tips of purple in the fall, and the habit is not as dense. 'Dallas Blues' has more arching foliage and a larger and broader habit. 'Gunsmoke' has more arching foliage, a broader habit, and the growth is slower. The new plant is taller in height than 'RR1' and slightly shorter in height than 'Shenandoah' but both 'RR1' and 'Shenandoah' develop reddish-purple or purplish-red leaf color in July and their habit is different. Table 1 below includes comparisons of other *Panicum* cultivars known to the inventor:

TABLE 1

| CULTIVAR | U.S. PLANT PAT. NO. | TOTAL HEIGHT | INITIAL COLOR |
|---|---|---|---|
| 'Apache Rose' | PP29,142 | 95 cm | gray green |
| 'Bad Hair Day' | PP29,313 | 210 cm | yellow green |
| 'Blue Fountain' | PP28,192 | 210 cm | blue green |
| 'Cape Breeze' | PP24,895 | 75 cm | dark green |
| 'Cheyenne Sky' | PP23,209 | 112 cm | blue green |
| 'Dallas Blues' | PP11,202 | 193 cm | grayed blue green |
| 'Gunsmoke' | PP32,373 | 135 cm | blue green |
| 'Haense Herms' | (not patented) | 100 cm | green |
| 'Heavy Metal' | (not patented) | 180 cm | blue green |
| 'Hot Rod' | PP26,074 | 90 cm | blue green |
| 'Northwind' | (not patented) | 180 cm | blue green |
| 'Prairie Fire' | PP19,367 | 100 cm | blue green |
| 'Rostrahlbush' | (not patented) | 110 cm | green |
| 'RR1' | PP17,944 | 120 cm | blue green |
| 'Shenandoah' | (not patented) | 140 cm | blue green |
| Smoking Gun' | current application | 136 cm | blue green |
| 'Thundercloud' | PP20,665 | 275 cm | blue green |
| 'Totem Pole' | PP29,951 | 200 cm | blue green |

| CULTIVAR | SEASONAL COLOR | SEASON OF CHANGE BEGINNING | HABIT |
|---|---|---|---|
| 'Apache Rose' | purple tipped | late July | dense upright |
| 'Bad Hair Day' | yellow green | none | upright |
| 'Blue Fountain' | blue green | none | upright |
| 'Cape Breeze' | purple tipped | late September | compact upright |
| 'Cheyenne Sky' | concord purple | early July | very upright |
| 'Dallas Blues' | purple tipped | late September | upright arching |
| 'Gunsmoke' | blue green | none | upright arching |
| 'Haense Herms' | red purple | early August | upright |
| 'Heavy Metal' | blue green | none | very upright |
| 'Hot Rod' | red purple | early spring | upright |
| 'Northwind' | yellow green | September | upright |
| 'Prairie Fire' | deep wine | early July | upright |
| 'Rostrahlbush' | red purple | early August | upright |
| 'RR1' | purple -red | early July | compact |
| 'Shenandoah' | red purple | late July | arching |
| Smoking Gun' | blue green | none | upright |
| 'Thundercloud' | blue green | none | arching upright |
| 'Totem Pole' | blue green | none | columnar |

The following traits of *Panicum* 'Smoking Gun', in combination, have been repeatedly observed in multiple generations of asexually propagated plants and distinguish the new plant from all other switch grass plants known to the inventor:

1. Dense, upright, highly-vigorous habit;
2. Consistent, airy, tan panicles make up over the top one-third of the plant;
3. Bluish-green, linear foliage retained throughout growing season with mostly upright to outwardly aspect and very little arching.

BRIEF DESCRIPTION OF THE DRAWINGS

The photograph of the new plant demonstrates the overall appearance of five-year-old plants growing in an outdoor trial garden in Zeeland, MI, including the unique traits. The colors are as accurate as reasonably possible with color reproductions. Ambient light spectrum, source and direction may cause the appearance of minor variation in color.

The FIGURE shows the overall plant in autumn.

DETAILED BOTANICAL DESCRIPTION

The following descriptions and color references are based on the 2015 edition of The Royal Horticultural Society Colour Chart except where common dictionary terms are used. The new plant, 'Smoking Gun', has not been observed in all possible environments. The phenotype may vary slightly with different environmental conditions, such as temperature, light, fertility, moisture and maturity levels, but without any change in the genotype. The following observations and descriptions are of a six-year-old plant in a loamy-sand trial garden of a wholesale perennial nursery in Zeeland, Michigan, USA, grown in full sun with supplemental water and fertilizer as needed.

Parentage: 17-6-x as the female (seed) parent and 17-2 as the male (pollen) parent;

Propagation method: By division of the culms;

Time to finishing in a 3.8-liter pot: Rapid; about 7 to 9 weeks from 25 mm diameter plug;

Rooting habit: Normal, coarsely branching; root color nearest RHS 155D;

Plant description:

Plant shape and habit: Hardy herbaceous perennial forming tightly rhizomatous columnar clump, with very upright culms topped with finely-textured airy inflorescence producing a narrow clump taller than wide;

Plant size: Foliage height at flowering time is about 136 cm tall from soil line to the top of the flowers; about 40 cm wide at soil line and about 90 cm at widest point about 45 cm above soil;

Foliage description: Linear; flat; margin with micro-dentations; sheathed from node of attachment to ligule, adaxial and abaxial surfaces dull, glabrous, glaucous; deciduous but persist through winter;

Foliage size: Blade to about 47.5 cm long and about 16 mm wide; sheath to about 15.5 cm long; average blade about 39 cm long and 14 mm wide; shorter at distal end; typically 6 leaves per culm;

Foliage color: Adaxial between RHS 137B and RHS 189A; abaxial between RHS 137B and RHS 189B; winter adaxial surface more grey than RHS 164D; winter abaxial surface between RHS 199D and RHS 164D;

Ligule: Irregularly fringed; to about 1 mm long; color nearest RHS 161A;

Veins: Parallel; midrib about 1 mm across; adaxial slightly recessed, abaxial costate;

Vein color: Adaxial lower one-third between RHS 191B and RHS 191C, distally between RHS 137B and RHS 189A; abaxial between RHS 137B and RHS 189B;

Culm: Erect; terete; hollow; glabrous; glaucous; dull surface; about 90% enclosed by leaf sheath; about 200 culms per clump;

Culm dimension: To about 100 cm long without panicle, average about 92 cm; about 5 mm diameter at base; internode length average about 11.5 cm;

Culm color: Where exposed between RHS N138A and RHS 188A;

Node description: About 6 per culm, slightly swollen to about 7 mm diameter;

Node color: Nearest RHS 195A;

Flower description: Finely-branched moderately-open panicle; one panicle per culm;

Flower timing: Beginning early August flowering through late August, panicles dry and remain effective through winter;

No flower fragrance detected;

Panicle: Oblong ellipsoidal; to about 37 cm long and 15 cm wide slightly above center; overall effective color nearest RHS 157A;

Rachis: Terete, branched, glabrous, glaucous; about 37 cm long and about 2.5 mm diameter at base; branches to about 15 cm long and about 1 mm diameter held at about 60 degree angle above horizontal; color between RHS N138A and RHS 122A;

Spikelet: Usually with two or three florets; about 10 to 12 mm long;

Rachilla: Thin, terete, stiff; to about 8 to10 mm long and about 0.2 mm diameter; color between RHS N138A and RHS 122A;

Lower glume: Subulate; about 2.5 mm long and 1 mm wide; without awn; color nearest RHS 193A;

Upper glume: Subulate; to about 3.5 mm long and 1 mm wide; without awn; color distally nearest RHS 147B and proximally nearest RHS 193A;

Lemma: Subulate; without awn or bristle; acute apex, truncate base; margin entire; upper and lower both about 2.5 mm long and 0.7 mm wide; color between RHS 138D and RHS 138C;

Palea: Subulate; acute apex without awn or bristle, truncate base, margin entire; about 2 mm long and 0.7 mm across; translucent to color between RHS 138D and RHS 138C;

Gynoecium: Two;

*Stigma*.—Two, plumose, protruding about 1.5 mm from glume and about 0.5 mm diameter; color nearest RHS 187A.

*Style*.—Thin; about 1 mm long and 0.1 mm diameter; color nearest RHS 155D.

*Ovary*.—Ellipsoidal; acute apex, rounded base; about 2 mm long and 1 mm diameter; color nearest RHS 146B.

Androecium: Two or three;

*Filaments*.—Short; hair-like; less than 0.1 mm diameter and up to 1 mm long; color nearest RHS NN155D.

*Anthers*.—Two; dorsifixed, longitudinal; about 2 mm long and about 0.5 mm wide; color nearest RHS 165A.

*Pollen*.—Round, abundant; less than 0.1 mm in diameter; nearly transparent, color nearest RHS N163A.

Fruit: Caryopsis; about 2.5 mm long and about 1 mm wide; color nearest RHS 161C;

Hardiness, pest and disease resistance: The plant is very drought tolerant once established. Hardiness at least from USDA zone 4 through 9. Disease and pest resistance beyond what is typical of that of other switch grasses has not been observed.

I claim:

1. A new and distinct cultivar of ornamental switch grass, *Panicum* plant named 'Smoking Gun', as herein described and illustrated.

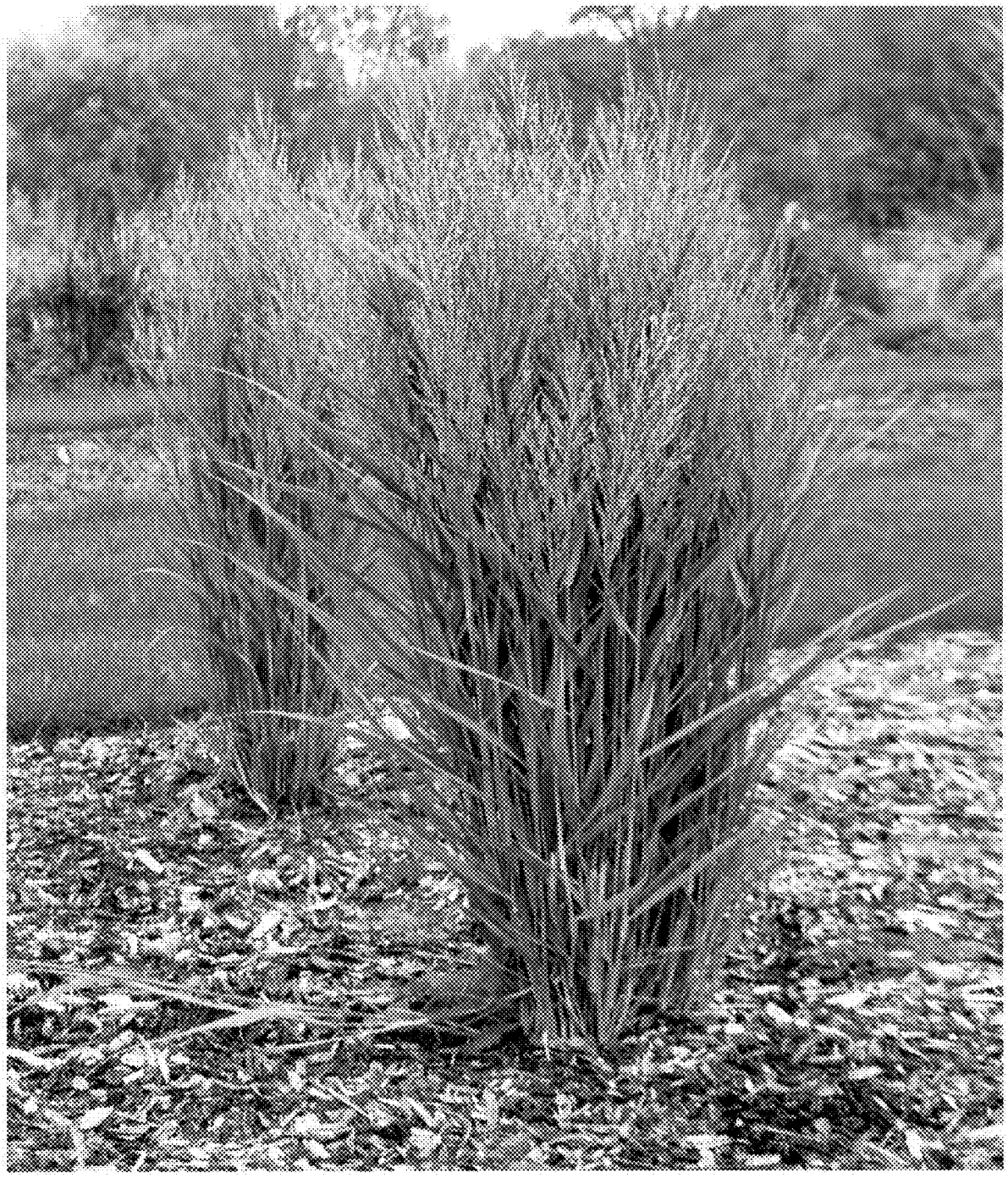

* * * * *